US010485604B2

United States Patent
Henne et al.

(10) Patent No.: US 10,485,604 B2
(45) Date of Patent: Nov. 26, 2019

(54) VAPOR TREATMENT OF LUNG NODULES AND TUMORS

(71) Applicant: Uptake Medical Technology Inc., Seattle, WA (US)

(72) Inventors: Erik Henne, Seattle, WA (US); Robert Lawrence Barry, Kirkland, WA (US); Robert Alan Mest, Long Beach, CA (US)

(73) Assignee: Uptake Medical Technology Inc., Seattle, WA (US)

( * ) Notice: Subject to any disclaimer, the term of this patent is extended or adjusted under 35 U.S.C. 154(b) by 867 days.

(21) Appl. No.: 14/957,433

(22) Filed: Dec. 2, 2015

(65) Prior Publication Data

US 2016/0151103 A1    Jun. 2, 2016

Related U.S. Application Data

(60) Provisional application No. 62/086,606, filed on Dec. 2, 2014.

(51) Int. Cl.
*A61B 18/04* (2006.01)
*A61B 18/00* (2006.01)

(52) U.S. Cl.
CPC .... *A61B 18/04* (2013.01); *A61B 2018/00541* (2013.01); *A61B 2018/00577* (2013.01); *A61B 2018/048* (2013.01)

(58) Field of Classification Search
CPC .............. A61B 18/04; A61B 2018/044; A61B 2018/046; A61B 2018/048; A61B 2018/00541; A61B 2018/00577; A61B 2018/00005; A61B 2018/00011; A61B 2018/0007; A61B 2018/00029; A61B 2018/00041; A61B 2018/00017
USPC .......... 606/20–22, 27; 604/26; 607/104, 105
See application file for complete search history.

(56) References Cited

U.S. PATENT DOCUMENTS

| 408,899 A | 8/1889 | Small |
|---|---|---|
| 1,719,750 A | 7/1929 | Bridge et al. |
| 3,880,168 A | 4/1975 | Berman |
| 4,026,285 A | 5/1977 | Jackson |
| 4,773,410 A | 9/1988 | Blackmer et al. |

(Continued)

FOREIGN PATENT DOCUMENTS

| AU | 721086 B2 | 6/2000 |
|---|---|---|
| EP | 1003582 B1 | 2/2003 |

(Continued)

OTHER PUBLICATIONS

Becker, et al.; Lung volumes before and after lung volume reduction surgery; Am J Respir Crit Care Med; vol. 157; pp. 1593-1599; (1998) Oct. 28, 1997.

(Continued)

*Primary Examiner* — Thomas A Giuliani
(74) *Attorney, Agent, or Firm* — Richard Batt

(57) ABSTRACT

Systems and methods for treating a lesion in a lung of a patient are described. Embodiments can include navigating a vapor exit port of a vapor delivery catheter to an airway point near a lung region in which the lesion resides, delivering condensable vapor from the vapor delivery catheter along anatomic boundaries of the lung region, and creating a uniform field of necrosis in tissue around the lesion by allowing the condensable vapor to condense.

17 Claims, 2 Drawing Sheets

(56) References Cited

U.S. PATENT DOCUMENTS

| | | |
|---|---|---|
| 4,793,352 A | 12/1988 | Eichenlaub |
| 4,915,113 A | 4/1990 | Holman |
| 4,950,266 A | 8/1990 | Sinofsky |
| 5,006,119 A | 4/1991 | Acker et al. |
| 5,011,566 A | 4/1991 | Hoffman |
| 5,084,043 A | 1/1992 | Hertzmann et al. |
| 5,112,328 A | 5/1992 | Taboada et al. |
| 5,158,536 A | 10/1992 | Sekins et al. |
| 5,263,951 A | 11/1993 | Spears et al. |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,424,620 A | 6/1995 | Cheon et al. |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,549,628 A | 8/1996 | Cooper et al. |
| 5,562,608 A | 10/1996 | Sekins et al. |
| 5,575,803 A | 11/1996 | Cooper et al. |
| 5,591,157 A | 1/1997 | Hennings et al. |
| 5,620,440 A | 4/1997 | Heckele et al. |
| 5,695,507 A | 12/1997 | Auth et al. |
| 5,735,811 A | 4/1998 | Brisken |
| 5,752,965 A | 5/1998 | Francis et al. |
| 5,755,753 A | 5/1998 | Knowlton |
| 5,782,914 A | 7/1998 | Schankereli |
| 5,800,482 A | 9/1998 | Pomeranz et al. |
| 5,824,703 A | 10/1998 | Clark, Jr. |
| 5,827,268 A | 10/1998 | Laufer |
| 5,913,856 A | 6/1999 | Chia et al. |
| 5,957,919 A | 9/1999 | Laufer |
| 5,964,752 A | 10/1999 | Stone |
| 5,972,026 A | 10/1999 | Laufer et al. |
| 5,986,662 A | 11/1999 | Argiro et al. |
| 5,989,445 A | 11/1999 | Wise et al. |
| 6,032,077 A | 2/2000 | Pomeranz |
| 6,053,909 A | 4/2000 | Shadduck |
| 6,059,011 A | 5/2000 | Giolo |
| 6,083,255 A | 7/2000 | Laufer et al. |
| 6,099,251 A | 8/2000 | LaFleur |
| 6,102,037 A | 8/2000 | Koch |
| 6,113,722 A | 9/2000 | Hoffman et al. |
| 6,130,671 A | 10/2000 | Argiro |
| 6,131,570 A | 10/2000 | Schuster et al. |
| 6,139,571 A | 10/2000 | Fuller et al. |
| 6,156,036 A | 12/2000 | Sussman et al. |
| 6,162,232 A | 12/2000 | Shadduck |
| 6,179,805 B1 | 1/2001 | Sussman et al. |
| 6,194,066 B1 | 2/2001 | Hoffman |
| 6,200,333 B1 | 3/2001 | Laufer |
| 6,210,404 B1 | 4/2001 | Shadduck |
| 6,219,059 B1 | 4/2001 | Argiro |
| 6,273,907 B1 | 8/2001 | Laufer |
| 6,283,988 B1 | 9/2001 | Laufer et al. |
| 6,283,989 B1 | 9/2001 | Laufer et al. |
| 6,299,633 B1 | 10/2001 | Laufer |
| 6,300,150 B1 | 10/2001 | Venkatasubramanian |
| 6,312,474 B1 | 11/2001 | Francis et al. |
| 6,327,505 B1 | 12/2001 | Medhkour et al. |
| 6,394,949 B1 | 5/2002 | Crowley et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,411,852 B1 | 6/2002 | Danek et al. |
| 6,458,231 B1 | 10/2002 | Wapner et al. |
| 6,468,313 B1 | 10/2002 | Claeson et al. |
| 6,488,673 B1 | 12/2002 | Laufer et al. |
| 6,493,589 B1 | 12/2002 | Medhkour et al. |
| 6,508,816 B2 | 1/2003 | Shadduck |
| 6,527,761 B1 | 3/2003 | Soltesz et al. |
| 6,575,929 B2 | 6/2003 | Sussman et al. |
| 6,579,270 B2 | 6/2003 | Sussman et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,652,594 B2 | 11/2003 | Francis et al. |
| 6,653,525 B2 | 11/2003 | Ingenito et al. |
| 6,669,694 B2 | 12/2003 | Shadduck |
| 6,676,628 B2 | 1/2004 | Sussman et al. |
| 6,679,264 B1 | 1/2004 | Deem et al. |
| 6,682,520 B2 | 1/2004 | Ingenito |
| 6,692,494 B1 | 2/2004 | Cooper et al. |
| 6,712,812 B2 | 3/2004 | Roschak et al. |
| 6,719,738 B2 | 4/2004 | Mehier |
| 6,755,794 B2 | 6/2004 | Soukup |
| 6,770,070 B1 | 8/2004 | Balbierz |
| 6,776,765 B2 | 8/2004 | Soukup et al. |
| 6,860,847 B2 | 3/2005 | Alferness et al. |
| 6,885,888 B2 | 4/2005 | Rezai |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,986,769 B2 | 1/2006 | Nelson et al. |
| 6,997,189 B2 | 2/2006 | Biggs et al. |
| 7,022,088 B2 | 4/2006 | Keast et al. |
| 7,027,869 B2 | 4/2006 | Danek et al. |
| 7,031,504 B1 | 4/2006 | Argiro et al. |
| 7,083,612 B2 | 8/2006 | Littrup et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,175,644 B2 | 2/2007 | Cooper et al. |
| 7,192,400 B2 | 3/2007 | Campbell et al. |
| 7,198,635 B2 | 4/2007 | Danek et al. |
| 7,233,820 B2 | 6/2007 | Gilboa |
| 7,235,070 B2 | 6/2007 | Vanney |
| 7,335,195 B2 | 2/2008 | Mehier |
| 7,347,859 B2 | 3/2008 | Garabedian et al. |
| 7,412,977 B2 | 8/2008 | Fields et al. |
| 7,422,563 B2 | 9/2008 | Roschak et al. |
| 7,422,584 B2 | 9/2008 | Loomas et al. |
| 7,425,212 B1 | 9/2008 | Danek et al. |
| 7,462,162 B2 | 12/2008 | Phan et al. |
| 7,628,789 B2 | 12/2009 | Soltesz et al. |
| 7,708,712 B2 | 5/2010 | Phan et al. |
| 7,740,017 B2 | 6/2010 | Danek et al. |
| 7,778,704 B2 | 8/2010 | Rezai |
| 7,815,590 B2 | 10/2010 | Cooper |
| 7,819,908 B2 | 10/2010 | Ingenito |
| 7,906,124 B2 | 3/2011 | Laufer et al. |
| 7,913,698 B2 | 3/2011 | Barry et al. |
| 7,985,187 B2 | 7/2011 | Wibowo et al. |
| 7,993,323 B2 | 8/2011 | Barry et al. |
| 8,002,740 B2 | 8/2011 | Willink et al. |
| 8,088,127 B2 | 1/2012 | Mayse et al. |
| 8,147,532 B2 * | 4/2012 | Barry ............... A61B 18/04 607/83 |
| 8,172,827 B2 | 5/2012 | Deem et al. |
| 8,187,269 B2 | 5/2012 | Shadduck et al. |
| 8,251,070 B2 | 8/2012 | Danek et al. |
| 8,292,882 B2 | 10/2012 | Danek et al. |
| 8,322,335 B2 | 12/2012 | Barry et al. |
| 8,585,645 B2 | 11/2013 | Barry et al. |
| 8,734,380 B2 * | 5/2014 | Barry ............... A61B 18/04 604/23 |
| 8,858,549 B2 | 10/2014 | Shadduck et al. |
| 8,900,223 B2 | 12/2014 | Shadduck |
| 9,050,076 B2 * | 6/2015 | Barry ............... A61B 18/04 |
| 9,113,858 B2 | 8/2015 | Barry et al. |
| 2002/0077516 A1 | 6/2002 | Flanigan |
| 2002/0111386 A1 | 8/2002 | Sekins et al. |
| 2002/0112723 A1 | 8/2002 | Schuster et al. |
| 2002/0177846 A1 | 11/2002 | Mulier et al. |
| 2003/0099279 A1 | 5/2003 | Venkatasubramanian et al. |
| 2003/0181922 A1 | 9/2003 | Alferness |

(56) References Cited

U.S. PATENT DOCUMENTS

| | | |
|---|---|---|
| 2004/0031494 A1 | 2/2004 | Danek et al. |
| 2004/0038868 A1 | 2/2004 | Ingenito |
| 2004/0047855 A1 | 3/2004 | Ingenito |
| 2004/0055606 A1 | 3/2004 | Hendricksen et al. |
| 2004/0068306 A1 | 4/2004 | Shadduck |
| 2004/0199226 A1 | 10/2004 | Shadduck |
| 2004/0200484 A1 | 10/2004 | Springmeyer |
| 2004/0244803 A1 | 12/2004 | Tanaka |
| 2005/0016530 A1 | 1/2005 | McCutcheon et al. |
| 2005/0066974 A1 | 3/2005 | Fields et al. |
| 2005/0166925 A1 | 8/2005 | Wilson et al. |
| 2005/0171396 A1 | 8/2005 | Pankratov et al. |
| 2005/0171582 A1 | 8/2005 | Matlock |
| 2005/0203483 A1 | 9/2005 | Perkins et al. |
| 2005/0215991 A1 | 9/2005 | Altman et al. |
| 2005/0222485 A1 | 10/2005 | Shaw et al. |
| 2006/0004400 A1 | 1/2006 | McGurk et al. |
| 2006/0047291 A1 | 3/2006 | Barry |
| 2006/0100619 A1 | 5/2006 | McClurken et al. |
| 2006/0130830 A1 | 6/2006 | Barry |
| 2006/0135955 A1 | 6/2006 | Shadduck |
| 2006/0162731 A1 | 7/2006 | Wondka et al. |
| 2006/0200076 A1 | 9/2006 | Gonzalez et al. |
| 2006/0224154 A1 | 10/2006 | Shadduck et al. |
| 2007/0032785 A1 | 2/2007 | Diederich et al. |
| 2007/0036417 A1 | 2/2007 | Argiro et al. |
| 2007/0068530 A1 | 3/2007 | Pacey |
| 2007/0091087 A1 | 4/2007 | Zuiderveld |
| 2007/0092864 A1 | 4/2007 | Reinhardt et al. |
| 2007/0102011 A1 | 5/2007 | Danek et al. |
| 2007/0106292 A1 | 5/2007 | Kaplan et al. |
| 2007/0109299 A1 | 5/2007 | Peterson |
| 2007/0112349 A1 | 5/2007 | Danek et al. |
| 2007/0118184 A1 | 5/2007 | Danek et al. |
| 2007/0137646 A1 | 6/2007 | Weinstein et al. |
| 2007/0293853 A1 | 12/2007 | Truckai et al. |
| 2008/0033493 A1 | 2/2008 | Deckman et al. |
| 2008/0132826 A1 | 6/2008 | Shadduck et al. |
| 2009/0018538 A1 | 1/2009 | Webster et al. |
| 2009/0043301 A1 | 2/2009 | Jarrard et al. |
| 2009/0138001 A1 | 5/2009 | Barry et al. |
| 2009/0149846 A1 | 6/2009 | Hoey et al. |
| 2009/0192508 A1 | 7/2009 | Laufer et al. |
| 2009/0216220 A1 | 8/2009 | Hoey et al. |
| 2009/0301483 A1* | 12/2009 | Barry ............... A61B 18/04 128/203.12 |
| 2009/0312753 A1 | 12/2009 | Shadduck et al. |
| 2010/0094270 A1 | 4/2010 | Sharma |
| 2010/0204688 A1 | 8/2010 | Hoey et al. |
| 2010/0256714 A1 | 10/2010 | Springmeyer |
| 2010/0262133 A1 | 10/2010 | Hoey et al. |
| 2011/0077628 A1 | 3/2011 | Hoey et al. |
| 2011/0160648 A1* | 6/2011 | Hoey ............... A61B 18/04 604/26 |
| 2011/0270031 A1 | 11/2011 | Frazier et al. |
| 2011/0301587 A1 | 12/2011 | Deem et al. |
| 2012/0016363 A1 | 1/2012 | Mayse et al. |
| 2012/0016364 A1 | 1/2012 | Mayse et al. |
| 2013/0006231 A1 | 1/2013 | Sharma et al. |
| 2013/0267939 A1* | 10/2013 | Barry ............... A61B 18/04 606/27 |
| 2015/0094607 A1* | 4/2015 | Barry ............... A61B 18/04 600/538 |
| 2015/0230852 A1 | 8/2015 | Barry et al. |
| 2017/0172640 A1* | 6/2017 | Henne ............... A61B 18/04 |

FOREIGN PATENT DOCUMENTS

| | | |
|---|---|---|
| EP | 1143864 B1 | 2/2004 |
| EP | 1173103 B1 | 10/2005 |
| EP | 1326549 B1 | 12/2005 |
| EP | 1326548 B1 | 1/2006 |
| EP | 1485033 B1 | 8/2009 |
| WO | WO 00/11927 A2 | 3/2000 |
| WO | WO 01/02042 A1 | 1/2001 |
| WO | WO 02/069821 A1 | 9/2002 |
| WO | WO 03/070302 A1 | 8/2003 |
| WO | WO 03/086498 A2 | 10/2003 |
| WO | WO 2005/025635 A2 | 3/2005 |
| WO | WO 2005/102175 A2 | 11/2005 |
| WO | WO 2006/003665 A2 | 1/2006 |
| WO | WO 2006/052940 A2 | 5/2006 |
| WO | WO 2006/053308 A2 | 5/2006 |
| WO | WO 2006/053309 A2 | 5/2006 |
| WO | WO 2006/080015 A2 | 8/2006 |
| WO | WO 2006/116198 A2 | 11/2006 |
| WO | WO 2008/051706 A2 | 5/2008 |
| WO | WO 2009/009236 A1 | 1/2009 |
| WO | WO 2009/009398 A1 | 1/2009 |
| WO | WO 2009/015278 A1 | 1/2009 |
| WO | WO 2009/137819 A1 | 11/2009 |
| WO | WO 2010/042461 A1 | 4/2010 |
| WO | WO 2011/056684 A2 | 5/2011 |
| WO | WO 2011/060200 A1 | 5/2011 |
| WO | WO 2011/060201 A1 | 5/2011 |
| WO | WO 2011/127216 A2 | 10/2011 |

OTHER PUBLICATIONS

Blacker, G. F.; Vaporization of the uterus; J. of Obstetrics and Gynaecology; vol. 33; pp. 488-511; (year of publication is sufficiently earlier than the effective U.S. filing date and any foreign priority date) 1902.

Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.

clinical trials.gov.; Study of the AeriSeal System for HyPerinflation Reduction in Emphysema; 4 pages; Nov. 5, 2014; retrieved from the internet (http://clinicaltrials.gov/show/NCT01449292).

Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).

Delaunois; Anatomy and physiology of collateral respiratory pathways; Eur. Respir. J.; 2(9); pp. 893-904; Oct. 1989.

Eyal et al.; The acute effect of pulmonary burns on lung mechanics and gas exchange in the rabbit; Br. J. Anaesth.; vol. 47; pp. 546-552; (year of publication is sufficiently earlier than the effective U.S. filing date and any foreign priority date) 1975.

Ferlay et al.; GLOBOCAN 2008 v1.2, Cancer Incidence and Mortality Worldwide: IARC CancerBase No. 10 [internet]; 16 pages; retrieved from the internet (http://www.iarc.fr/en/media-centre/iarcnews/2010/GLOBOCAN2008.pdf); Lyon, France: International Agency for Research on Cancer; Jun. 1, 2010.

Fishman et al., A randomized trial comparing lung-volume-reduction surgery with medical therapy for severe emphysema, N Engl J Med, vol. 348, No. 21, pp. 2059-2073, May 22, 2003.

Goldberg et al.; Radiofrequency tissue ablation in the rabbit lung: Efficacy and complications; Acad. Radiol.; vol. 2; pp. 776-784; Sep. 1995.

Herth et al.; Efficacy predictors of lung volume reduction with zephyr valves in a european cohort; Eur. Respir. J.; 39(6); pp. 1334-1342; Jun. 2012.

Homasson, et al., "Bronchoscopic cryotherapy for airway strictures caused by tumors," Chest, vol. 90, No. 2, pp. 159-164, Aug. 1986.

Kang, Li, "Efficient optimal net surface detection for image segmentation—from theory to practice," M.Sc. Thesis, The University of Iowa, Dec. 2003.

Kinsella et al.; Quantitation of emphysema by computed tomography using a "densitymask" program and correlation with pulmonary function tests; Chest; 97(2); pp. 315-321; Feb. 1990.

Looga, R. U.; Mechanism of changes in the respiratory and cardiovascular reflexes from the lungs associated with intrapulmonary steam burns; Eng. Trans. from Byulleten Eksperimental noi Biologii I Meditsiny; vol. 61; No. 6; pp. 31-33; Jun. 1966.

Marasso, et al., "Cryosurgery in bronchoscopic treatment of tracheobronchial stenosis," Chest, vol. 103, No. 2, pp. 472-474, Feb. 1993.

(56) References Cited

OTHER PUBLICATIONS

Marasso, et al., "Radiofrequency resection of bronchial tumours in combination with cryotherapy: evaluation of a new technique," Thorax, vol. 53, pp. 106-109, (year of publication is sufficiently earlier than the effective U.S. filing date and any foreign priority date) 1998.
Mathur et al., Fiberoptic bronchoscopic cryotherapy in the management of tracheobronchial obstruction, Chest, vol. 110, No. 3, pp. 718-723, Sep. 1996.
Morice et al.; Endobrinchial argon plasma coagulation for treatment of hemotysis and neoplastic airway obstruction, Chest, vol. 119, No. 3, pp. 781-787, Mar. 2001.
Moritz et al.; The effects of inhaled heat on the air pasage and lungs; American Journal of Pathology; vol. XXI; pp. 311-331; (year of publication is sufficiently earlier than the effective U.S. filing date and any foreign priority date) 1944.
Moulding et al.; Preliminary studies for achieving transcervical oviduct occlusion by hot water or low-pressure steam; Advances in Planned Parenthood; vol. 12, No. 2; pp. 79-85; (year of publication is sufficiently earlier than the effective U.S. filing date and any foreign priority date) 1977.
National Lung Screening Trial Research Team; Reduced lung-cancer mortality with low-dose computed tomographic screening; N. Eng. J. Med.; 365(5); pp. 395-409; Aug. 4, 2011.
Pracht, Adam, "VIDA takes new approach," Iowa City Press-Citizen, Sep. 12, 2005.
Quin, Jacquelyn, "Use of neodymium yttrium aluminum garnet laser in long-term palliation of airway obstruction," Connecticut Medicine, vol. 59, No. 7, pp. 407-412, Jul. 1995.
Sciurba et al.; A randomized study of endobronchial valves for advanced emphysema; N. Eng. J. Med.; 363(13); pp. 1233-1244; Sep. 23, 2010.
Shah et al.; Collateral ventilation and selection of techniques for bronchoscopic lung volume reduction; Thorax; 67(4); pp. 285-286; Apr. 2012.
Slebos et al.; Bronchoscopic lung volume reduction coil treatment of patients with severe heterogeneous emphysema; Chest; 142(3); pp. 574-582; Sep. 2012.
Sutedja, et al.; Bronchoscopic treatment of lung tumors; Elsevier, Lung Cancer, 11, pp. 1-17, Jul. 1994.
Tschirren et al.; Intrathoracic airway trees: segmentation and airway morphology analysis from low-dose CT scans; IEEE Trans. Med. Imaging; vol. 24, No. 12; pp. 1529-1539; Dec. 2005.
Tschirren, Juerg; Segmentation, anatomical labeling, branchpoint matching, and quantitative analysis of human airway trees in volumetric CT images; Ph.D. Thesis; The University of Iowa; Aug. 2003.
Tschirren, Juerg; Segmentation, anatomical labeling, branchpoint matching, and quantitative analysis of human airway trees in volumetric CT images; Slides from Ph.D. defense; The University of Iowa; Jul. 10, 2003.
Van De Velde; Vapo-cauterization of the uterus; Amer. J. Med. Sci.; vol. CXVIII; (year of publication is sufficiently earlier than the effective U.S. filing date and any foreign priority date) 1899.
Vorre et al.; Morphology of tracheal scar after resection with CO2-laser and high-frequency cutting loop; Acta Otolaryngol (Stockh); vol. 107; pp. 307-312; (year of publication is sufficiently earlier than the effective U.S. filed and any foreign priority date) 1989.

\* cited by examiner

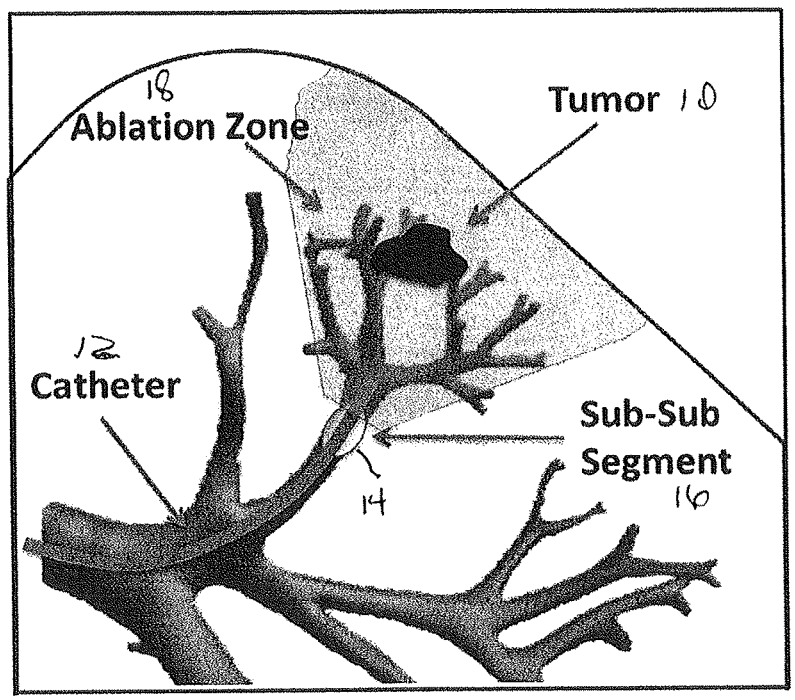
FIG. 1
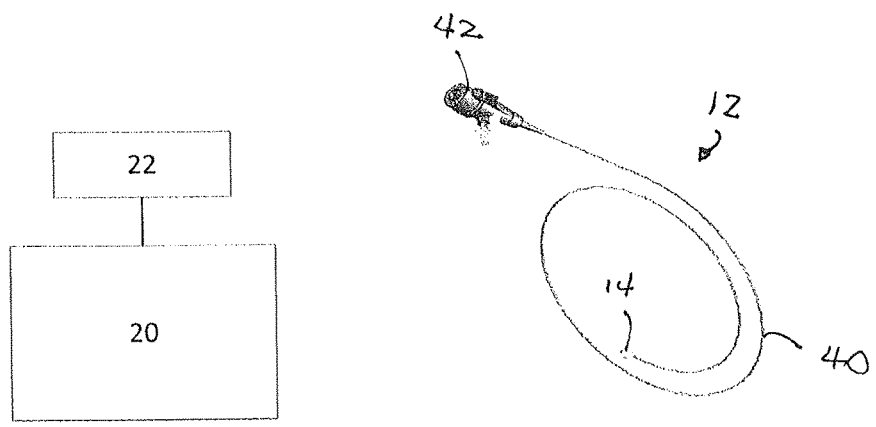
FIG. 2A
FIG. 2B

VAPOR TREATMENT OF LUNG NODULES AND TUMORS

CROSS-REFERENCE TO RELATED APPLICATIONS

This application claims the benefit of U.S. Provisional Appln. No. 62/086,606, titled "Vapor Treatment of Lung Nodules and Tumors", filed on Dec. 2, 2014, which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Over 1.8 million people worldwide were diagnosed with lung cancer in 2012. In the US, approximately 400,000 individuals are living with lung cancer and 225,000 new cases are expected to be diagnosed in 2014, comprising 13% of all cancer diagnoses. Most patients with lung cancer are elderly. In 2010, 82% with lung cancer were older than 60. It is estimated that in the US, lung cancer care costs $12.1 billion. More males are living with lung cancer than women (66.8 and 49.2 per 100,000) in the U.S., however, this difference is converging.

The survival rate of lung cancer is much lower than the other leading cancer locations, with a five-year survival rate of 16.6% compared to 64.2% for colon, 89.2% for breast, and 99.2% for prostate. More than 50% of people with lung cancer die within one year of being diagnosed. This poor survival rate has been mainly attributed to the fact that by the time a person with lung cancer becomes symptomatic, the cancer has metastasized and is in the later stages.

Recent screening programs to detect and treat lung cancer earlier have helped to improve the prognosis of people with lung cancer. The National Lung Screening Trial demonstrated that screening with low-dose computed tomography (CT) reduces mortality by 20% in certain high risk populations. Screening finds nodules sooner where they are less likely to have metastasized.

Surgery is currently the treatment of choice for patients with early stage non-small cell lung cancer (NSCLC), which can often achieve cure through the resection alone. The aim with surgery is to remove the entire tumor including a margin, typically about 2 cm of normal tissue surrounding the tumor. Different surgical approaches are commonly used, such as wedge resection, segmentectomy, lobectomy, or pneumonectomy. Which technique is used depends on the nodule characteristics, the patient's physiological reserve, and the surgeon's skill. Many of these patients have significant comorbidities and are therefore at risk of morbidity, mortality and resultant high resource utilization. Additionally, the lungs are a frequent site of metastatic disease, in 20% of cases it is the only site. Especially in patients with oligometastatic disease, surgery is part of the conventional treatment strategy. Many of these patients have high comorbidities and are non-surgical candidates.

38% of patients undergoing a resection experience major complications, including arrhythmias, prolonged air leaks, prolonged chest tube drainage and infection. A study of 7,000 patients showed a mortality rate of 1.3% for lung resections in general and 3.2% for pneumonectomies. Successful surgery often is associated with a loss of exercise capacity in the range of 10-40%, which can significantly affect quality of life. Post-resection pain can persist for four years and occurs in approximately 30% of patients. 5% of patients experience severe disabling pain. All of these complications and risk of mortality and morbidity increase in older patients and patients with comorbidities.

CT-guided percutaneous ablation in the form of radiofrequency (RF) ablation, microwave ablation, or cryotherapy are being explored as an alternative method of treating these tumors in non-surgical patients. However, none of these techniques have been successfully adapted for bronchoscopic application. Among the challenges faced by these various energy based devices is the difficulty in navigating to and penetrating the lesion, as well as the ability to take a consistent margin. In addition, these approaches are relatively lengthy (10-60 minutes per energy application) and often lead to pneumothorax. Moreover, it is difficult to ablate the entire tumor or nodule, along with a tissue margin around the tumor or nodule, with these therapies.

Condensable vapor has been delivered to the region in and around the lungs for other therapeutic purposes. For example, U.S. Pat. No. 7,892,229 describes the injection of heated water vapor into a volume of the lung distal to an occluding balloon for the purpose of shrinking and collapsing the lung tissue to reduce lung volume. The therapy results in shrinkage of collagenous tissues in the airway walls, leading to fibrosis and permanent sealing of the treated airways. The '229 patent does not address the use of condensable vapor to treat tumors or nodules in the lung, and it does not disclose how one would use the described apparatus to treat lung tumors or nodules.

U.S. Pat. Nos. 7,913,698; 8,147,532; and 8,322,335 all describe the delivery of condensable vapor to the lung to treat COPD, tumors or nodules. None of these patents describes devices or therapies specifically tailored to treat lung tumors or nodules, and none identifies a vapor delivery protocol that causes tumor or nodule tissue to necrose without also causing charring and/or thermal fixing of the tissue in and around the tumor or nodule.

SUMMARY OF THE DISCLOSURE

An outpatient procedure performed by a bronchoscopist to treat lung tumors and nodules has the potential to improve mortality and morbidity, have less breathing impairment, lower costs, and improve quality of life as compared to surgery. A bronchoscopic technique could feasibly be used for treatment of early stage lung cancer in the same procedure as the diagnosis, further reducing the treatment impact on the patient.

For the purposes of this disclosure, "treatment" is an intervention aimed at changing the nature or character of tissue, including necrosing tissue, debulking tissue, and/or initiating an immune response directed toward tissue.

For the purposes of this disclosure, "lesion" means a tissue abnormality, such as a primary lung cancer tumor, a metastatic nodule, a pre-cancerous or possibly cancerous nodule.

The present invention relates to a lung therapy method specifically adapted to treat lesions in the lung, such as nodules and cancerous tumors. One aspect of the invention provides a method of treating a lesion in a lung of a patient. In some embodiments, the method includes the steps of navigating a vapor exit port of a vapor delivery catheter to an airway point near a lung region (e.g., lung subsegment or sub-subsegment) in which the lesion resides; delivering condensable vapor from the vapor delivery catheter along anatomic boundaries of the lung region; and creating a uniform field of necrosis in tissue around the lesion by allowing the condensable vapor to condense. The method may also include the step of isolating the lung region distal to the airway branching point prior to delivering the vapor. Allowing the vapor to condense may also cause necrosis of the lesion.

In some embodiments, the method creates a uniform field of necrosis in tissue around the lesion without charring or thermally fixing the tissue. In some embodiments, 270-450 calories of energy are transferred from the condensable vapor to the tissue.

The method and system of this invention provide a minimally invasive bronchoscopic treatment for ablating lesions in the lung of patients with primary lung cancer or metastases. The potential benefits of this approach over other interventional approaches are:

Minimally invasive (not percutaneous);

Delivery of therapy to the parenchyma via the bronchi (no need to pierce nodule);

Compatible with peripheral navigation systems;

Outside-in treatment; ablation includes margin similar to resection;

Treatment includes all of the lesion-related lung segment(s) but respects natural anatomical boundaries; and Shorter procedure times.

A method of treating a lesion in a lung of a patient is provided, the method comprising navigating a vapor exit port of a vapor delivery catheter to an airway point near a lung region in which the lesion resides, delivering condensable vapor from the vapor delivery catheter along anatomic boundaries of the lung region, and creating a uniform field of necrosis in tissue around the lesion by allowing the condensable vapor to condense.

In one embodiment, the lung region is a subsegment of the lung. In another embodiment, the lung region is a sub-subsegment of the lung.

In some embodiments, the creating step comprises creating a uniform field of necrosis in tissue around the lesion without charring the tissue. In other embodiments, the creating step comprises creating a uniform field of necrosis in tissue around the lesion without thermally fixing the tissue. In additional embodiments, the creating step further comprises transferring 270-450 calories of energy from the condensable vapor to the tissue.

In some embodiments, the method further comprises isolating the lung region distal to the airway branching point prior to the delivering step.

A method of treating a lesion in a lung of a patient is also provided, the method comprising delivering condensable vapor from a vapor delivery catheter directly into parenchyma of a lung region in which the lesion resides, and creating a uniform field of necrosis in tissue around the lesion by allowing the condensable vapor to condense.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 is a schematic representation of method of this invention.

FIGS. 2A-B show components of a vapor generation and delivery system that may be used to practice the lung therapies of this invention.

DETAILED DESCRIPTION

Figure 4:
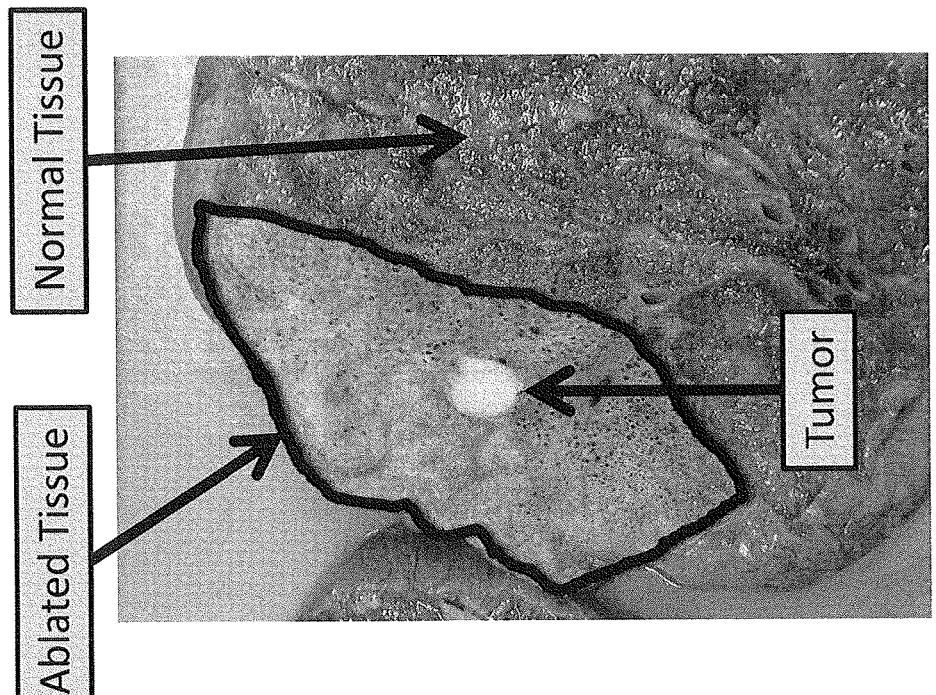
FIG. 4 is a photograph of an ex vivo human lung showing an ablated tissue boundary containing a tumor following treatment along the method of this invention.

The method of the invention is illustrated in FIG. 1. After identification of a tumor, nodule or other lesion 10 in the lung, water vapor is delivered via catheter 12 to an airway that ventilates the region, i.e., the parenchyma surrounding a lesion. Catheter 12 may be advanced through a bronchoscope (not shown) having, e.g., a 2.0 mm or larger working channel. A balloon 14 in the airway proximal to the lesion isolates that portion of the airway (here, a sub-subsegment 16 of the lung) so that the water vapor will extend only distally from the balloon. The water vapor follows the channels of the lung that naturally transport gas (inhaled air, exhaled carbon dioxide) and condenses to deliver a concentrated amount of thermal energy to the lung tissue in the isolated region (e.g., subsegment, sub-subsegment) during its phase change from gas to liquid. This application of thermal energy causes an acute injury to the tissues in the isolated lung, resulting in necrosis in the ablation zone 18.

Because of the unique ability of this thermal energy in gas form to convect through the natural airspaces, the entire parenchyma fed by the bronchus is affected. However, because the gas is not readily transported to the parenchyma across anatomical boundaries, neighboring parenchyma and other tissue is minimized. Ablation to neighboring tissue occurs only through conduction, which is limited to approximately 1 mm in the treatment time delivered, because of the short duration of the treatment. Thus, the ablative effects are limited by anatomic boundaries to the ablation zone 18. The most effective treatment extends the necrotic effect to the boundaries of the isolated lung region.

Ablation of the parenchyma surrounding a lesion causes cell death, thrombosis of the arteries and veins, and destruction of the lymphatic system. As a result of this uniform field of necrosis, healing can only occur from the "outside of the field in" because all transport channels to the "inside of the field" are destroyed. As a result, any portions of a lesion within that field that were not directly ablated by the condensing vapor will necrose over time as a result of the ablation of the tissue adjacent to the lesion and the resulting ischemia of the region.

Because the architectural structure of the ablated tissue is largely left intact, acute changes are minimal. The tissue is not thermally fixed and can therefore be reabsorbed during the natural healing process, including the lesion itself. This targeted bronchoscopic ablation of lung lesions completely destroys lung lesions in a quick and minimally invasive manner with limited effect on breathing mechanics and neighboring tissue. In addition, because of the limited damage to the tissue in the isolate region, scar tissue formation is minimized to reduce false positives in later X-ray or CT images of the lung region.

FIGS. 2A-B show components of a vapor generation and delivery system for use with this invention. The system may include a vapor generator 20 with an input mechanism 22

(such as, e.g., a graphic user interface) to enter control parameters (e.g., power level, water flow rate and treatment duration). The system connects to catheter 12 via a connector 42 to deliver vapor from the generator 20 to the patient.

In the illustrated embodiment, catheter 12 has a shaft 40 extending from a hub 42 through compliant balloon 14 to a distal opening. Catheter 12 has separate lumens for the water vapor and for the balloon inflation fluid. In some embodiments, balloon 14 is formed from silicone and can be expanded to occlude a 10 mm diameter airway.

The system shown in FIGS. 2A-B may be used to treat lesions and surrounding tissue in an isolated lung region using condensable water vapor. In some embodiments, the power, water flow and treatment time may be selected by the user via the user interface on the generator. Exemplary settings for treatment of lung tumors and lung nodules are shown in Table 1 below:

TABLE 1

| Energy | Power Setting | Flow Setting | Time |
| --- | --- | --- | --- |
| 270 ± 20 calories | 600 watts | 9,000 μl/min | 8 seconds |
| 330 ± 20 calories | 700 watts | 10,500 μl/min | 8 seconds |
| 390 ± 20 calories | 800 watts | 12,000 μl/min | 8 seconds |
| 450 ± 20 calories | 900 watts | 13,500 μl/min | 8 seconds |

Delivery of 270-450 calories of energy to the isolate lung region over 8 seconds will provide uniform tissue necrosis in that region along the anatomic boundaries of the isolate airway.

In some embodiments, prior to treatment, the patient's lung will be imaged in a high resolution CT scan. The images may be evaluated using CT 3D reconstruction software (such as, e.g., the Broncus LungPoint system, the Covidien® superDimension™ navigation system or the Veran Medical Technologies SPiNView® system) to develop a treatment plan, including optimal treatment locations that will target lesions and the parenchyma around them. This treatment plan will take into account the navigational accessibility of the bronchoscope and vapor catheter. Similar software may also be used during the ablation procedure to assist with navigating the vapor catheter to the target locations by, e.g., manually matching the image reconstruction to live bronchoscopic camera images.

Example 1

The ability to create a uniform field of tissue necrosis in a lung segment (including lung subsegments and sub-subsegments) was examined in animal tests. Of routinely studied large animals, the pig lung is the most similar to the human lung in terms of airway diameters and volumes. However, it differs from human lungs with respect to the absence of collateral ventilation between sub-segmental regions. This lack of collateral ventilation in the pig lung creates a closed path which restricts venting of the segment during vapor delivery.

A total of 11 Yorkshire pigs were used in this study, including 3 females and 8 castrated males. The average weight at the time of treatment was 56.6 kg (range: 46.4-67 kg). For each treatment, a bronchoscope was used to navigate to the segment, the catheter described above with reference to FIG. 2 was placed in the airway under visual guidance via the bronchoscope, and the balloon was inflated to seal the airway.

After the end of the survival period, the pigs were sacrificed and a limited necropsy was performed on each animal. The isolated lungs were perfused with saline via the trachea in order to stiffen the tissue and cross-sectional slices were made of each treated segment. Photographs of each cross-section were taken, photographed, and gross findings noted. The tissue cross-sections were fixed in formalin and representative sections of treated lung parenchyma as well as sections from a control untreated segment were placed in tissue cassettes for tissue processing. The sections were paraffin embedded and sectioned, and stained with hematoxylin and eosin (H&E) stain.

Figure 3:
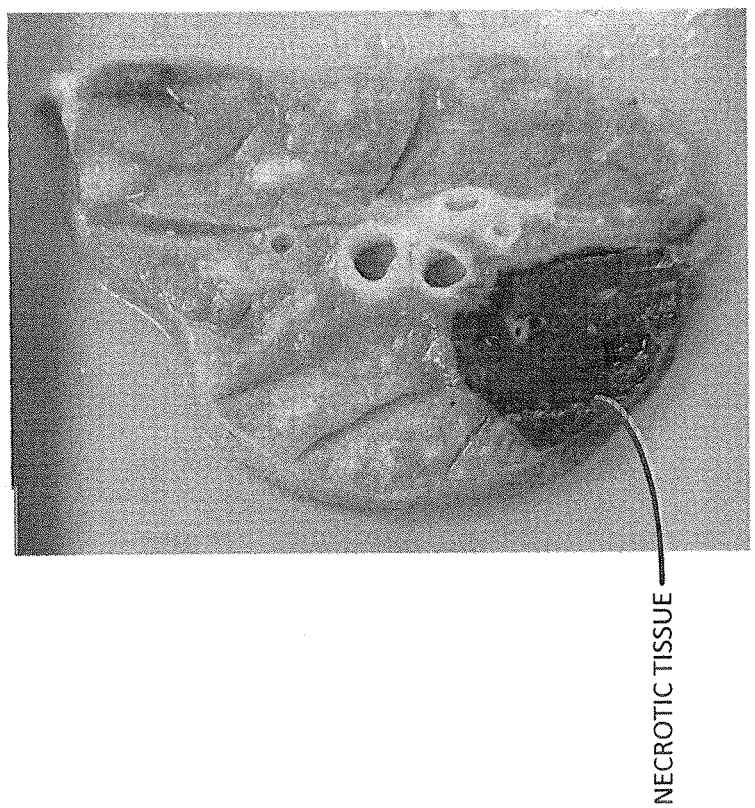
FIG. 3 is a photograph showing uniform necrosis in a lung subsegment of a pig following treatment along the method of this invention.

The primary endpoint for efficacy of treatment was the presence of uniform necrosis of the isolated lung region, which was assessed both by gross pathology as well as by histopathology. FIG. 3 is a photograph showing uniform necrosis (the dark area marked "necrotic tissue") in subsegment LV4 of one of the pigs.

Table 2 shows the energy delivered in to an isolated pig lung segment during a treatment and the percentage of the treated segments where uniform necrosis of the lung tissue was achieved.

TABLE 2

TABLE 2: The number and percentage of treated segments with uniform necrosis in pig lung per treatment power as assessed by gross pathology

| Energy | # of | Uniform Necrosis | |
| --- | --- | --- | --- |
| (calories) | treatments* | N | % of treatments |
| 125 ± 20 | 6 | 0 | 0 |
| 270 ± 20 | 27** | 12 | 44 |
| 330 ± 20 | 16 | 14 | 88 |
| 360 ± 20 | 14 | 11 | 79 |
| 390 ± 20 | 12 | 9 | 75 |

These data show that, in the energy range studied (125-390 calories), this technique resulted in tissue necrosis in the isolated lung region. The uniformity of necrosis varied with treatment power, with improving uniformity at higher energy levels up to a point (here, 330 calories), and energy levels beyond that point did not improve uniformity of necrosis outcomes.

Example 2

The system described above with respect to FIG. 2 was used to deliver 57 treatments to 6 ex vivo pig lungs at 3 different energy levels. The uniformity of the collagen denaturation was characterized to establish potential for efficacy at various energy levels. Each treatment to the ex vivo tissue causes collagen denaturation. It takes more heat to denature collagen than it does to permanently kill living tissue. Therefore collagen denaturation is a suitable marker for tissue that would be non-vital after treatment if it were in vivo.

The collagen denaturation boundary due to ablation was characterized to be either well-defined or not well-defined. Vapor is constrained by the anatomy to which it is delivered. A well-defined ablation boundary includes the pleural surface and has sharp edges that follow segmental divisions. The best treatment result is one that has a uniform effect and has a distinct boundary that reaches the pleural surface; a distinct boundary suggests that the entire sub-segment was affected by the vapor. Table 3 shows the primary endpoints for all treatments delivered.

TABLE 3

| Energy (calories) | Uniform Ablation | Ablation Boundary |
|---|---|---|
| 270 ± 20 | 29/43 (67%) | 26/43 (60%) |
| 330 ± 20 | 8/8 (100%) | 8/8 (100%) |
| 390 ± 20 | 4/6 (67%) | 4/6 (67%) |

The frequency of achieving a completely uniform effect in ex-vivo porcine was 67% at the lowest energy level tested of 270 calories. The frequency of achieving a well-defined boundary at 270 calories was 60%. This result is very similar to what was found in pig in vivo where 57% of comparable treatments achieved a completely uniform effect. (Boundary was not characterized in vivo). At higher energy levels, frequency of uniform ablation with well-defined boundary appeared to increase.

Example 3

The system described above with respect to FIG. 2 was used to deliver 63 treatments to 5 ex vivo canine lungs at 5 different energy levels. The uniformity of the collagen denaturation was characterized to establish potential for efficacy at various energy levels. Ablation uniformity (collagen denaturation due to ablation characterized to be either homogenous or to have degrees of heterogeneity) and ablation boundary (collagen denaturation boundary due to ablation was characterized to be either well-defined or not well-defined). Vapor is constrained by the anatomy it is delivered to. A well-defined ablation boundary includes the pleural surface and has sharp edges that follow segmental divisions. An energy range of 125 to 450 calories at 8 seconds was evaluated. Table 4 summarizes the primary endpoints for all treatments delivered.

TABLE 4

| Energy (calories) | Uniform Ablation | Ablation Boundary |
|---|---|---|
| 125 ± 20 | 9/10 (90%) | 4/10 (40%) |
| 270 ± 20 | 13/13 (100%) | 13/13 (100%) |
| 330 ± 20 | 9/9 (100%) | 9/9 (100%) |
| 390 ± 20 | 15/15 (100%) | 15/15 (100%) |
| 450 ± 20 | 15/15 (100%) | 15/15 (100%) |

These data show that the frequency of achieving a completely uniform effect was very consistent in the energy range of 270 to 450 calories with 100% of treatments achieving uniform effect. At the very low end of the energy range (125 calories), 90% of all treatments achieved completely uniform effect. Ablation boundary also had 100% achieving full boundary in the range 270 to 450 calories and 40% at the lowest energy level of 125 calories. These fields of ablation followed anatomical boundaries despite the presence of collateral ventilation.

Example 4

The system described above with respect to FIG. 2 was used to deliver 135 treatments to 10 ex vivo human lungs at 5 different energy levels. The 10 ex vivo human lungs treated in the study included normal lungs, lungs with emphysema, lungs with primary lung cancer, and lungs with metastatic lung cancer. Collagen denaturation in the tissue and tissue destruction was characterized to evaluated energy delivery efficacy and potential safety issues. Results were used to establish feasibility of the technique in human tissue; demonstrate the ability to create a uniform field of ablation around lung lesions; evaluate for other unexpected effects; and evaluate effects across an energy range. As in earlier studies, ablation uniformity and ablation boundary were the primary endpoints. Table 5 summarizes the endpoints for single 8 second treatments at different energy levels. FIG. 4 is a photograph of one of the ex vivo lungs showing an ablated tissue boundary containing a tumor.

TABLE 5

| Energy (calories) | Uniform Ablation | Ablation Boundary |
|---|---|---|
| 125 ± 20 | 2/3 (67%) | 1/3 (33%) |
| 270 ± 20 | 15/28 (54%) | 13/28 (46%) |
| 330 ± 20 | 26/36 (72%) | 24/36 (67%) |
| 390 ± 20 | 22/25 (88%) | 17/25 (68%) |
| 450 ± 20 | 14/15 (93%) | 13/15 (87%) |

Table 6 summarizes the frequency of achieving a uniform ablation correlated with the diameter of the airway at the point of isolation of the treated lung region.

TABLE 6

| Energy (calories) | 2.0 mm | 2.5 mm | 3.0 mm | 3.5 mm | 4.0 mm |
|---|---|---|---|---|---|
| 125 ± 20 | | | 1/1 (100%) | | 1/2 (50%) |
| 270 ± 20 | 0/1 (0%) | 1/4 (25%) | 10/15 (67%) | | 4/8 (50%) |
| 330 ± 20 | | 1/1 (100%) | 19/26 (73%) | 3/3 (100%) | 3/6 (50%) |
| 390 ± 20 | | 1/1 (100%) | 16/18 (89%) | | 5/6 (83%) |
| 450 ± 20 | | 1/1 (100%) | 5/6 (83%) | 1/1 (100%) | 7/7 (100%) |

Table 7 summarizes the frequency of achieving a uniform ablation correlated with bronchus generation.

TABLE 7

| Energy (calories) | $2^{nd}$ | $3^{rd}$ | $4^{th}$ | $5^{th}$ | $6^{th}$ |
|---|---|---|---|---|---|
| 125 ± 20 | | | | | |
| 270 ± 20 | | 2/6 (33%) | 7/9 (78%) | 1/1 (100%) | |
| 330 ± 20 | 5/6 (83%) | 14/20 (70%) | 6/8 (75%) | 1/1 (100%) | |
| 390 ± 20 | 3/4 (75%) | 8/10 (80%) | 3/3 (100%) | | 1/1 (100%) |
| 450 ± 20 | 3/3 (100%) | 7/8 (88%) | 4/4 (100%) | | |

These data show that the frequency of achieving completely uniform thermal effect with a clear boundary increased with energy. Smaller airway diameters at higher bronchus generations also achieved higher rates of treatment uniformity and clear boundaries.

While the preceding discussion focused on the delivery of vapor to the lungs as primary treatment, vapor therapy can also be used as an adjunct or adjuvant to other therapies to, e.g., improve the efficacy of another therapy modality (by, for example, stiffening the tissue through collagen denaturization), improve the outcome of the overall intervention, delay the timing of another intervention, etc.

In some embodiments of the invention, vapor may be delivered directly into the parenchyma via a catheter, needle or other conduit using, e.g., approaches described in U.S. 2013/0267939. In this embodiment, as in the earlier embodiments, delivery of the condensable vapor into the parenchyma creates a uniform field of necrosis without charring or thermally fixing the tissue.

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. A method of treating a lesion in a lung of a patient, the method comprising: navigating a vapor exit port of a vapor delivery catheter along an airway and to a point near a lung region in which the lesion resides, and in which the lung region can be isolated from a portion of the airway, wherein the lung region comprises a lung segment, subsegment or sub-subsegment having segmental boundaries encompassing both the lesion and healthy tissue surrounding the lesion and extending to the segmental boundaries; delivering condensable vapor from the exit port of the vapor delivery catheter for a first treatment time into said lung region sufficient to create a uniform field of necrosis in the lesion, the healthy tissue around the lesion and along said segmental boundaries by allowing the condensable vapor to condense; and determining, prior to the step of delivering, a first amount of energy to cause said uniform field of necrosis in the healthy tissue around the lesion, and to cause a well-defined ablation boundary between the uniform field of necrosis in the healthy tissue around the lesion and healthy non-targeted tissue along the segmental boundaries; and wherein the determining step is based on an airway diameter at said point.

2. The method of claim 1 wherein the lung region is a subsegment of the lung.

3. The method of claim 1 wherein the lung region is a sub-subsegment of the lung.

4. The method of claim 1 wherein the delivering step comprises creating the uniform field of necrosis in healthy tissue around the lesion without charring this healthy tissue.

5. The method of claim 1 wherein the delivering step comprises creating the uniform field of necrosis in healthy tissue around the lesion without thermally fixing this healthy tissue.

6. The method of claim 1 wherein the delivering step comprises transferring 270-450 calories of energy from the condensable vapor to the lesion and healthy tissue around the lesion.

7. The method of claim 6 wherein the first treatment time is 8 seconds.

8. The method of claim 1 further comprising isolating the lung region from the portion of the airway at said point by expanding a balloon in the airway at said point.

9. The method of claim 1 wherein the first amount of energy is further correlated with bronchus generation.

10. The method of claim 1 wherein the first amount of energy ranges from 125 to 330 calories.

11. The method of claim 1 wherein the step of delivering limits a depth of ablation of neighboring healthy non-targeted tissue to approximately 1 mm from the well-defined ablation boundary.

12. A method of treating a lesion in a lung of a patient, the method comprising: navigating a vapor exit port of a vapor delivery catheter along an airway and to an isolation point near a lung sub-segment in which the lesion resides, and in which the lung sub-segment can be isolated from a portion of the airway, the lung sub-segment having segmental divisions encompassing both the lesion and tissue surrounding the lesion; delivering condensable vapor from the exit port of the vapor delivery catheter into said lung sub-segment sufficient to create a uniform ablation in tissue around the lesion and along said segmental divisions; determining, prior to the step of delivering, a correlated first amount of energy sufficient to cause (a) said uniform ablation in tissue around the lesion and along said segmental divisions and (b) a distinct collagen denaturation boundary that follows the segmental divisions; and wherein the first amount of energy is based on diameter of the airway at the point of isolation of the lung subsegment.

13. The method of claim 12, wherein the first amount of energy is further correlated with bronchus generation.

14. The method of claim 12, wherein the boundary includes pleural surfaces.

15. The method of claim 12, wherein the step of delivering limits a depth of ablation of healthy non-targeted tissue to approximately 1 mm from the distinct collagen denaturation boundary.

16. The method of claim 12, wherein the first amount of energy ranges from 270 to 450 calories.

17. The method of claim 16, wherein the step of delivering has a duration of 8 seconds.

* * * * *